(12) United States Patent
Mohr

(10) Patent No.: US 12,403,028 B2
(45) Date of Patent: Sep. 2, 2025

(54) SOCK ORTHOTIC

(71) Applicant: Bio-Design, LLC, Palm Springs, CA (US)

(72) Inventor: Robert Neal Mohr, Palm Springs, CA (US)

(*) Notice: Subject to any disclaimer, the term of this patent is extended or adjusted under 35 U.S.C. 154(b) by 0 days.

(21) Appl. No.: 18/365,813

(22) Filed: Aug. 4, 2023

(65) Prior Publication Data
US 2024/0050258 A1 Feb. 15, 2024

Related U.S. Application Data

(60) Provisional application No. 63/474,333, filed on Aug. 9, 2022.

(51) Int. Cl.
| A61F 5/01 | (2006.01) |
| A41B 11/00 | (2006.01) |
| A41B 11/02 | (2006.01) |
| A41D 13/06 | (2006.01) |
| A43B 1/04 | (2022.01) |
| A61F 5/30 | (2006.01) |
| A61F 13/06 | (2006.01) |

(52) U.S. Cl.
CPC .......... *A61F 5/0111* (2013.01); *A41B 11/007* (2013.01); *A41B 11/02* (2013.01); *A41D 13/06* (2013.01); *A43B 1/04* (2013.01); *A61F 5/30* (2013.01); *A61F 13/064* (2013.01)

(58) Field of Classification Search
CPC ........ A61F 5/0111; A61F 5/30; A61F 13/064; A61F 5/0127; A61F 5/019; A61F 5/14; A61F 5/32; A41B 11/007; A41B 11/02; A41B 11/003; A41D 13/06; A43B 1/04; A43B 3/0036; A43B 7/14–149; D04B 1/02; D04B 1/102; D04B 1/26; D04B 1/265
USPC ............... 602/23, 27; 66/185–187; 2/239
See application file for complete search history.

(56) References Cited

U.S. PATENT DOCUMENTS

| 5,307,522 A * | 5/1994 | Throneburg ............ D04B 1/26 2/241 |
| 5,560,226 A * | 10/1996 | Throneburg ............ D04B 1/26 66/178 R |
| 7,587,915 B2 * | 9/2009 | Kaneda ................. D04B 1/102 66/185 |
| 9,439,457 B2 | 9/2016 | Baravarian |
| 10,149,500 B2 | 12/2018 | Baravarian |
| 10,362,811 B2 | 7/2019 | Baravarian |
| 11,186,930 B2 | 11/2021 | Huffa et al. |
| 11,576,441 B2 | 2/2023 | Baravarian |
| 2008/0041113 A1 * | 2/2008 | Mori ....................... D04B 1/26 66/171 |

(Continued)

OTHER PUBLICATIONS

Kevin Orthopedic, Catalog, Sep. 2018, 75 pages.
(Continued)

*Primary Examiner* — Rachael E Bredefeld
*Assistant Examiner* — Seth R. Brown
(74) *Attorney, Agent, or Firm* — Dergosits & Noah LLP

(57) ABSTRACT

A knit sock orthotic is provided in which a pattern of padding is knit into the sock to create an interface between the foot and the shoe or weight-bearing surface to correct an abnormal biomechanical condition of the foot, or to relieve pressure on focal areas of structural overload of the foot, or both.

10 Claims, 9 Drawing Sheets

(56) References Cited

U.S. PATENT DOCUMENTS

| | | | | |
|---|---|---|---|---|
| 2010/0331749 | A1* | 12/2010 | Powaser | A61F 5/0111 602/23 |
| 2014/0058311 | A1* | 2/2014 | Higgins | A61F 13/06 602/63 |
| 2014/0276321 | A1* | 9/2014 | Sellitto | A61F 5/0127 602/29 |
| 2015/0201703 | A1* | 7/2015 | Baravarian | A41B 11/003 2/239 |
| 2016/0166419 | A1* | 6/2016 | Jones | A43B 7/1445 602/66 |
| 2017/0056231 | A1* | 3/2017 | Hara | A61F 5/0111 |
| 2018/0207035 | A1* | 7/2018 | Gaither | D04B 1/265 |
| 2019/0167462 | A1* | 6/2019 | Shaffer | A61F 5/0127 |
| 2022/0071807 | A1* | 3/2022 | Salloum | A61F 13/066 |
| 2022/0125129 | A1* | 4/2022 | Blecha | D04B 1/26 |
| 2022/0257824 | A1* | 8/2022 | Romo, Jr. | D04B 1/265 |
| 2023/0151517 | A1* | 5/2023 | Matter | A41B 11/14 12/142 W |

OTHER PUBLICATIONS

Kevin Orthopedic, Clinical Foot Orthotic Prescribing Guide, 2019, 133 pages.

ArchTek, "The ArchTek Sock Explained," https://www.archteksocks.com/pages/archtek-technology, accessed Aug. 4, 2023, 1 page.

* cited by examiner

SOCK ORTHOTIC

CROSS-REFERENCE TO RELATED CASES

This application claims priority to U.S. Provisional Patent Application No. 63/474,333, entitled "Sock Orthotic," filed on Aug. 9, 2023, which is hereby incorporated by reference.

BACKGROUND

The human foot is so well designed and engineered that when it functions in an ideal or neutral position, with the subtalar joint neutral and the midtarsal joint locked, it requires little or no muscle activity to support us. Unfortunately, many feet cannot and do not function in their optimal positions due to compensation for biomechanical abnormalities that are inherited and expressed.

For most purposes, an "ideal" foot is one which, in its neutral position, functions with the back of the heel bone relatively vertical while the horizontal level of the forefoot bones rests on the flat ground, with each of the five metatarsal heads bearing its fair share of load. This relatively perpendicular relationship between the horizontal forefoot and the vertical rearfoot, in neutral position, is largely determined during the growing years due to developmental torsion of the talus bone in the ankle.

If the talus does not torque enough, the forefoot will be inverted or higher on the inside, relative to the rearfoot. Obviously, one cannot function with the inside of the forefoot above the ground, so the rearfoot subtalar joint compensates to lower the arch by pronation of the subtalar joint. If the talus torques too much, the inside edge of the forefoot would be lower than the outside, requiring the rearfoot subtalar joint to compensate by supination, or rolling outwards. Deviations on either side of "ideal" result in a foot that functions sub-optimally, requiring additional muscular support and subjecting it to overuse symptoms. In any case, compensation of the rearfoot subtalar joint will occur by necessity to position the forefoot horizontally on the flat ground surface.

In addition to biomechanical compensation symptoms, deviations away from "ideal" may result in abnormally high focal areas of pressure from a metatarsal that may be structurally too low or long, or from a joint that may be excessively mobile so that it does not assume its fair share of weight distribution. Over time, these areas are subjected to mechanical overload resulting in subsequent inflammation and pain.

Fortunately, all these problems are well understood, and treatment modalities exist to compensate for biomechanical abnormalities. Successful intervention typically requires that therapeutic efforts be directed to the causative conditions which, if properly addressed, result in resolution of symptoms.

The range of currently available biomechanical therapy includes application of tape support, wedging to compensate for excessive pronation or supination, and padding to alleviate areas of focal pressure overload. If basic therapy is effective, the problem may be solved with wedge or pad placement in shoes or with over-the-counter supports. If more sophisticated therapy is necessary, a prescription orthotic may be designed and fabricated to better control abnormal biomechanical compensation and/or accommodate for areas of pressure overload. Such pads may be known by a number of names including, e.g.: cushion, correction, orthotic pad, shoe insert pad, biomechanical pad, biomechanical correction, and corrective pad.

However, such solutions are often unsatisfactory, creating a significant gap in patient compliance because they are shoe specific and occupy space within footgear. Not all shoes tolerate orthotics and orthotics take up space in shoes. Furthermore, existing cushioned socks only provide a general increase in softness.

Thus, what is needed is an orthotic device that remains with the foot, provides a therapeutic interface for the foot, and is easily transferrable.

BRIEF DESCRIPTION OF THE DRAWINGS

The embodiments are illustrated by way of example and not limitation in the accompanying drawings, in which like references indicate similar elements, and in which.

DETAILED DESCRIPTION

Embodiments described within disclose a sock orthotic that fills a gap in existing therapeutic modalities by providing a specific biomechanical interface between the foot and the shoe or the foot and the ground. In embodiments, the sock orthotic utilizes specific pad configurations having differential areas of thickness that are intrinsically knit into the pattern of the sole of the sock, creating: 1) wedging corrections to provide biomechanical control and/or 2) focal build-ups to reduce pressure overload on adjacent anatomical structures.

Embodiments of a sock orthotic incorporate biomechanical orthotic corrections into a sock manufactured utilizing pad configurations having varying degrees of intrinsically woven thicknesses and patterns within the bottom contour of the sock. By wearing such embodiments, a user may reduce or eliminate specific lower extremity symptoms, benefitting from an interface that effectively controls, compensates for, or accommodates abnormal biomechanical function or uneven structural pressure distribution in the foot. In addition, embodiments may be available over-the-counter and may be recommended by health-care practitioners or selected by the users based on their presenting symptoms.

Thus, embodiments vary greatly from existing socks that only have areas of uniform thickness for padding, or that rely on elastic compression for support (e.g., such as Archtek socks).

Figures 1, 2, 3, 4:
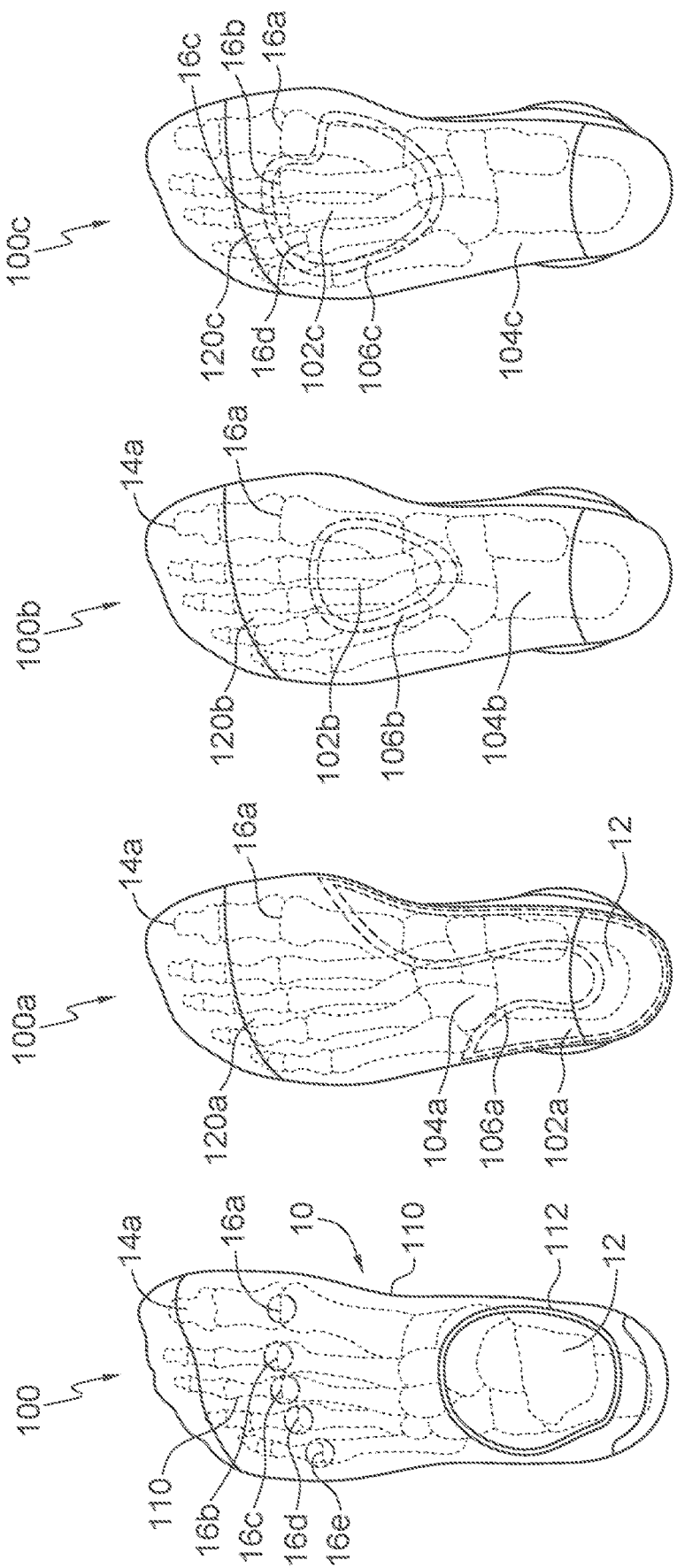
FIG. 1 is a top view of an embodiment of a sock orthotic.
FIG. 2 is a bottom view of an embodiment of a sock orthotic with a cobra pad configuration.
FIG. 3 is a bottom view of an embodiment of a sock orthotic with a metatarsal pad configuration.
FIG. 4 is a bottom view of an embodiment of a sock orthotic with a dancer's pad configuration.

FIG. 1 is a top view of an embodiment of a sock orthotic 100 on a left foot 10. In FIG. 1, sock 100 includes a sock upper 110 with an opening 112. Sock upper 110 is shown partially transparent to reveal the position of foot 10, for reference. Foot 10 includes phalanges 14a . . . 14e, joints 16a . . . 16e, and an attached ankle 12. Sock upper 110, of FIG. 1 is common to all embodiments. In embodiments, right sock orthotics and left sock orthotics that have the same type of orthotic padding are mirror images of each other and the description of one applies equally to the other.

FIG. 2 is a bottom view of an embodiment 100a of a sock orthotic including a pad section 102a with a cobra pad configuration, and with the sock rendered partially transparent to reveal foot 10 within. In FIG. 2, which illustrates the right-side version, sock orthotic 100a includes a sole 120a. Sole 120a includes a base sole section 104a, a transition section 106a, and a padded section that, in this embodiment is cobra pad section 102a. Base sole section 104a includes a knit and a thickness that serves as a baseline for the sole thickness. Transition section 106a indicates a section in which the thickness of the sock transitions from the thickness of sole section 104a, to the increased thickness of the padded section, i.e., cobra pad section 102a. Cobra pad section 102a is roughly "J" shaped such that it curls about the perimeter of the heel and extends forward along the arch toward the great toe joint 16a. FIG. 2 shows sock 100a from the bottom and the increase in thickness of cobra pad section 102a extends upward toward the foot, or into the page. A cobra pad is designed to reduce central plantar heel pain and provide support for the arch, for the purpose of alleviating the symptoms of plantar fasciitis, heel spurs and arch pain.

FIG. 2 illustrates, as do FIG. 3-FIG. 7B, how the embodiment of the sock orthotic, when properly worn, positions and retains the orthotic pad section at the proper placement with respect to the foot. These figures also illustrate that the orthotic pad section, being integrated into the sock, travels with the sock and, therefore, may be easily transferred to different footwear with the position of the orthotic unchanged with respect to the foot. Also, the sock orthotic may be used without footwear, with the sock creating an interface between the foot and the floor.

For convenience, in embodiments, each separate embodiment will be labeled 100n, each sole with be labeled 120n, each padded section will be labeled 102n, each base sole section will be labeled 104n, and each transition section will be labeled 106n, where "n" is a letter and common for a particular embodiment and its elements.

FIG. 3 is a bottom view of an embodiment 100b of a sock orthotic including a pad section 102b with a metatarsal pad configuration. Sock orthotic 100b is rendered partially transparent to reveal foot 10 within. In FIG. 3, which illustrates the right-side version, sock orthotic 100b includes a sole 120b. Sole 120b includes a base sole section 104b, a transition section 106b, and a padded section that, in this embodiment is metatarsal pad section 102a. Base sole section 104b includes a knit and a thickness that serves as a baseline for the sole thickness (as do all base sole sections 104n). Transition section 106b indicates a section in which the thickness of the sock transitions from the thickness of sole section 104b, to the increased thickness of the padded section, i.e., metatarsal pad section 102b (as do all transition sections 106n). Metatarsal pad section 102b is roughly triangularly shaped such that it extends from behind joints 16a . . . 16d to the mid-arch. FIG. 3 shows sock 100b from the bottom and the increase in thickness of metatarsal pad section 102b extends upward toward the foot, or into the page, as do all pads 102n in FIG. 2-FIG. 8B. However, in embodiments, a pad may be knit such that it extends downward from the sock sole and away from the foot. Similarly, in embodiments, a pad may be knit such that the increase in thickness extends both upward toward the foot and downward away from the foot. A metatarsal pad is designed to reduce focal pressure on the metatarsal heads by providing a step-up in thickness from the arch to just behind the metatarsal heads; utilized to alleviate metatarsalgia, capsulitis and neuroma symptoms.

FIG. 4 is a bottom view of an embodiment 100c of a sock orthotic including a pad section 102c with a dancer's pad configuration. Sock orthotic 100c is rendered partially transparent to reveal foot 10 within. In FIG. 3, which illustrates the right-side version, sock orthotic 100c includes a sole 120c. Sole 120c includes a base sole section 104c, a transition section 106c, and a padded section that, in this embodiment is dancer's pad section 102c. Dancer's pad section 102c is roughly fist shaped such that it lies beneath joints 16b . . . 16d but not joint 16a. Dancer's pad section 102c extends generally to the mid-arch. A dancer's pad is designed to reduce focal pressure beneath the great toe joint 16a by providing a step-up in thickness adjacent to the symptomatic area; utilized to alleviate sesamoiditis and pain under the great toe joint.

Figure 5A:
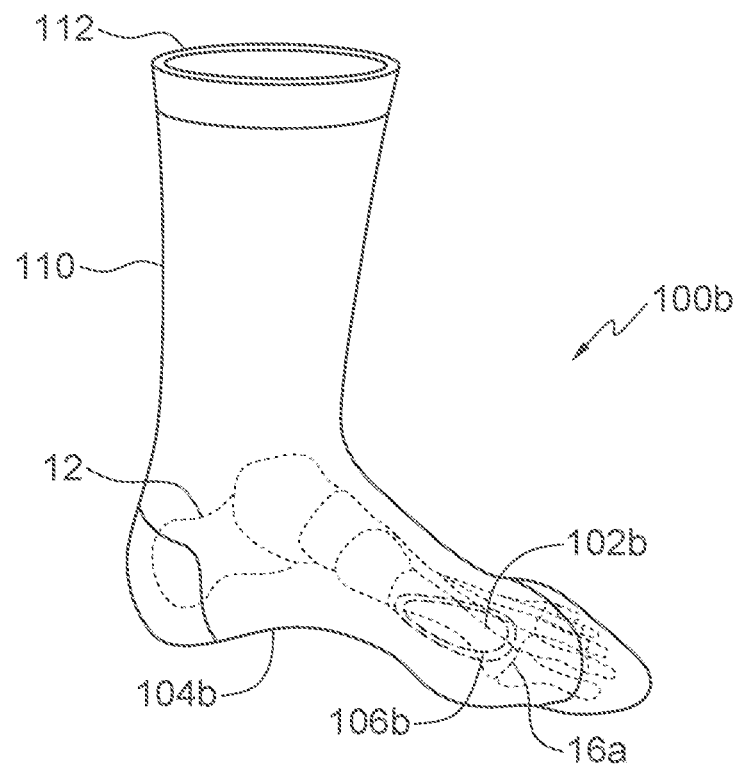
FIG. 5A is an upper front left perspective view of an embodiment of a sock orthotic for the left foot with a metatarsal pad configuration.
Figure 5B:
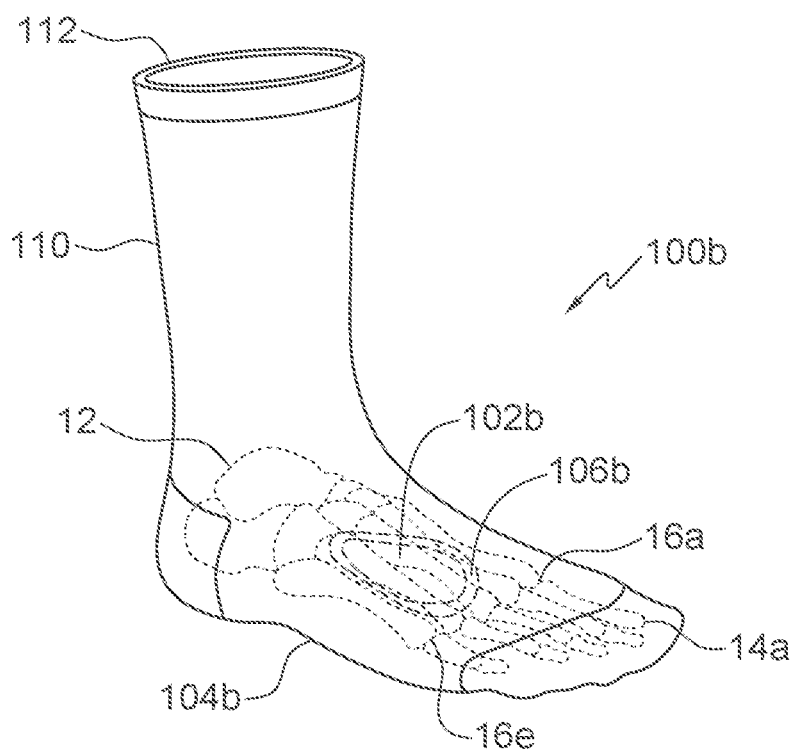
FIG. 5B is an upper front left perspective view of an embodiment of a sock orthotic for the right foot with a metatarsal pad configuration.

FIG. 5A and FIG. 5B are upper front left perspective views of left-foot and right-foot versions, respectively, of sock orthotic 100b. FIG. 5A and FIG. 5B further illustrate the shape of metatarsal pad section 102b and its location with respect to foot 10.

Figure 6A:
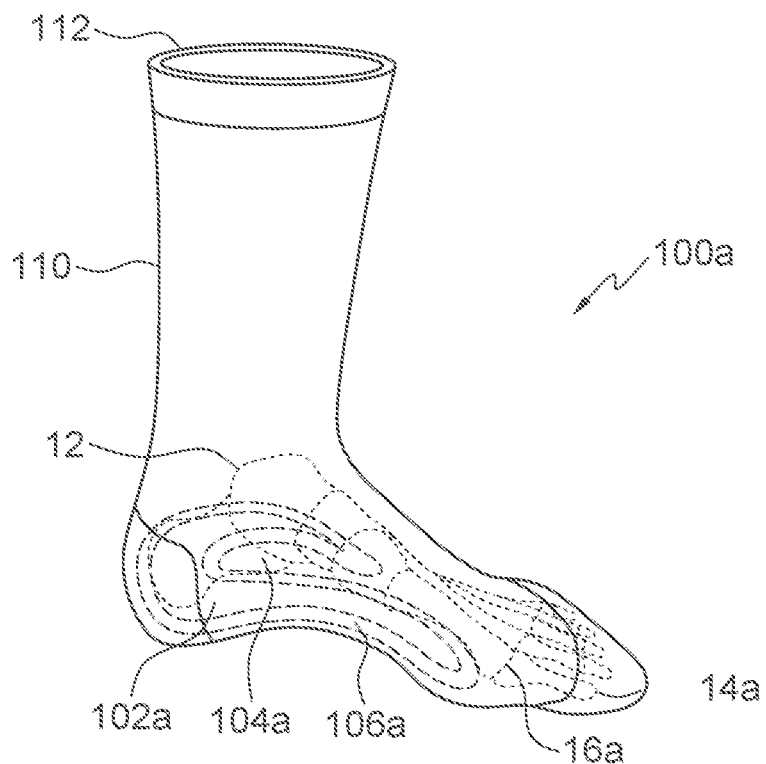
FIG. 6A is an upper front left perspective view of an embodiment of a sock orthotic for the left foot with a cobra pad configuration.
Figure 6B:
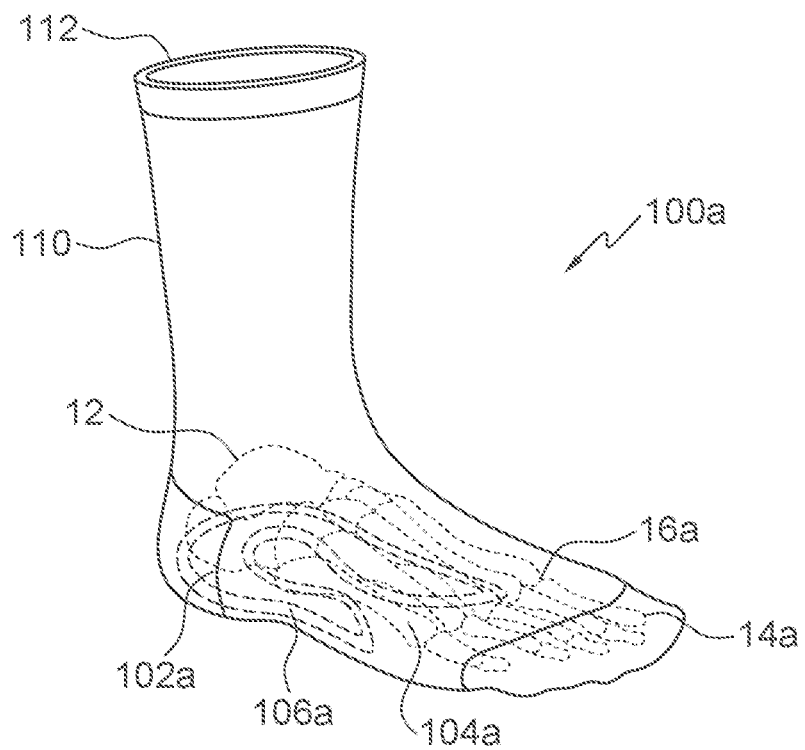
FIG. 6B is an upper front left perspective view of an embodiment of a sock orthotic for the right foot with a cobra pad configuration.

FIG. 6A and FIG. 6B are upper front left perspective views of left-foot and right-foot versions, respectively, of sock orthotic 100a. FIG. 6A and FIG. 6B further illustrate the shape of cobra pad section 102a and its location with respect to foot 10.

Figure 7A:
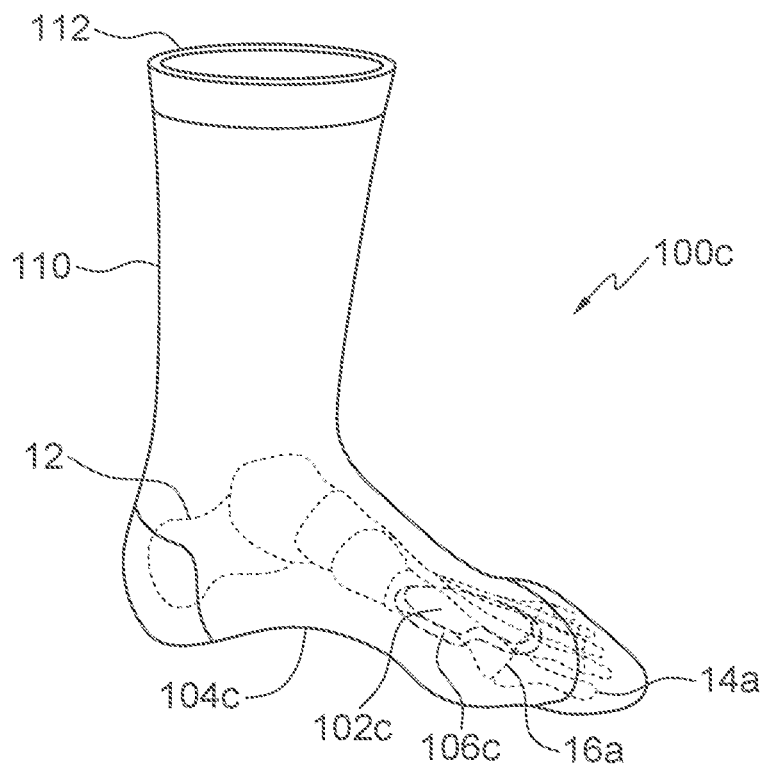
FIG. 7A is an upper front left perspective view of an embodiment of a sock orthotic for the left foot with a dancer's pad configuration.
Figure 7B:
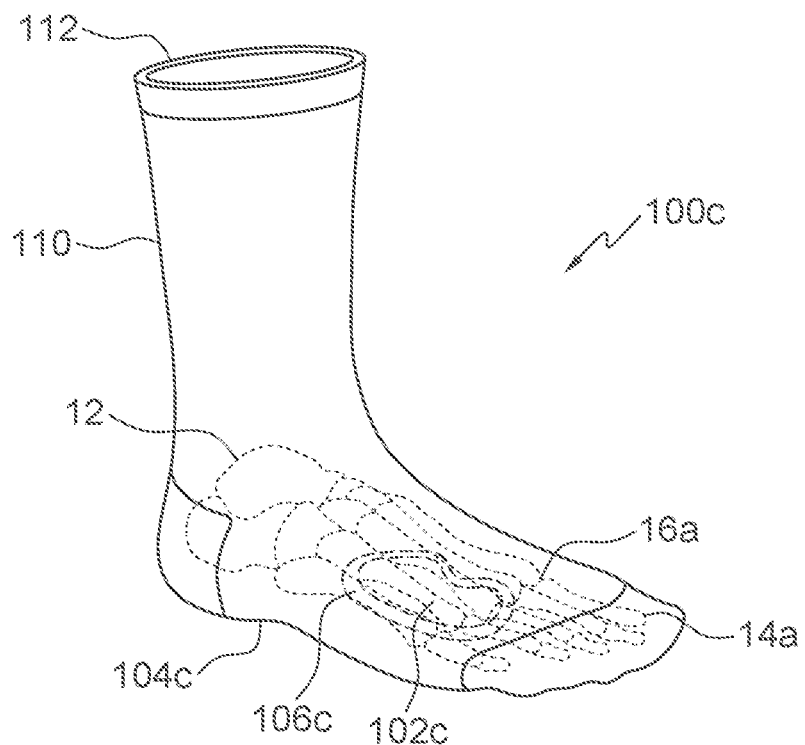
FIG. 7B is an upper front left perspective view of an embodiment of a sock orthotic for the right foot with a dancer's pad configuration.

FIG. 7A and FIG. 7B are upper front left perspective views of left-foot and right-foot versions, respectively, of sock orthotic 100c. FIG. 7A and FIG. 7B further illustrate the shape of dancer's 102c and its location with respect to foot 10.

Figure 8A:
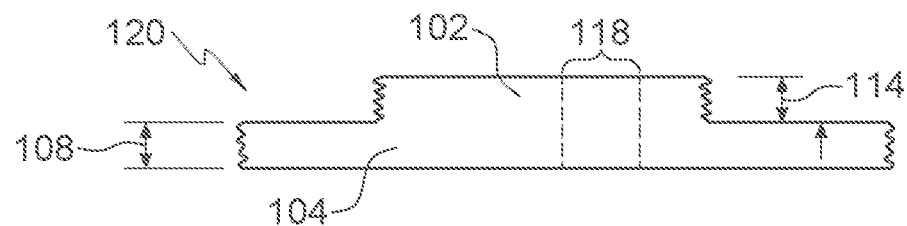
FIG. 8A is a side view illustrating aspects of an embodiment of a sock orthotic.

FIG. 8A is a side view illustrating aspects of an embodiment of a sock orthotic. In FIG. 8A, base sock section 104 has a base thickness 108 and padded section 102 has an extra padded thickness 114 (or "accommodation thickness"). Extra padded thickness 114 is added by increasing the thickness of the knitting of sole 120. Thus, extra padded section 102 is integrated into the weave of sole 120. Extra padded thickness 114 may represent the thickness of any of the embodiments of padded section 102n. In some embodiments, extra padded thickness is at least 0.125", which is considered to be a minimum effective thickness. However, in embodiments, extra padded thickness 114 may be varied as required across the shape of the pad. In embodiments, the non-therapeutic area base sock thickness 108 may be comparable to a traditional athletic sock. In an embodiment, an extra padded section 102 may include a subsection, a pattern pad 118, that has an increased density compared to the remainder of padded section 102. In an embodiment, extra padded thickness 114 may represent a thickness when measured under load, i.e., extra padded thickness 114 may be intended to be, e.g., 0.125" when bearing the user's weight, but is configured such that it is greater than 0.125" when unloaded and 0.125" when compressed with the user's anticipated weight. For example, in an embodiment a correlation may be made between a sock size and an estimated user weight. Also, in an embodiment, a plurality of socks for a particular shoe size may be provided, with each sock in the plurality configured to compress to a desired pad thickness for a user within a specific weight range.

Figure 8B:
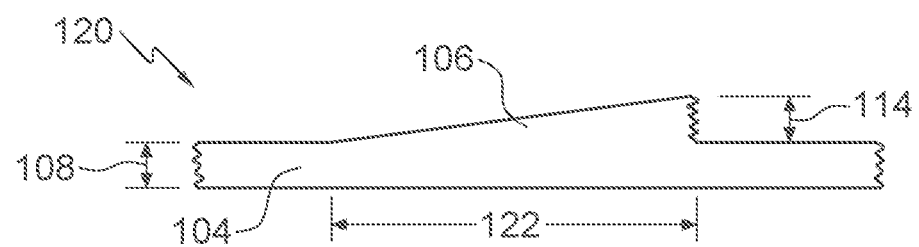
FIG. 8B is a side view illustrating aspects of an embodiment of a sock orthotic.

FIG. 8B is a side view illustrating aspects of an embodiment of a sock orthotic. In FIG. 8B, base sock section 104 has a base thickness 108 and a transition section 106 that ramps up to extra padded thickness 114 over a distance 122. As in FIG. 8A, extra padded thickness 114 is added by gradually increasing the thickness of the knitting of sole 120. Thus, transition section 102 is integrated into the knit of sole 120. Extra padded thickness 114 may represent the thickness of any of the embodiments of transition section 106n. As shown in FIG. 2-FIG. 7B, distance 122 may vary between the various transition sections, and even within the same transition section. Thus, the rate at which the thickness of transition section 106 increases may vary as needed to create a desired transition profile. Similarly, the rate at which the thickness of transition section 106 increases may also vary with the result being that transition sections may have non-linear profiles that may include, e.g.: abrupt step changes, gradually increasing slopes, abruptly increase slopes that taper to a flat, and gradually increasing slopes that change to gradually levelling-off slopes.

As shown in FIG. 8B, the total thickness of a sole 120 may be adjusted as needed, e.g., from a base thickness 108 to the sum of base thickness 108 and extra padded thickness 114. Thus, in some embodiments, the thicknesses of transition sections 106n and padded sections 102n may be arbitrarily changed as needed. This may include configurations in which the thickness of the pad may be less than base thickness 108, such as "cut-out" areas designed to reduce focal concentrations of pressure. In some such configurations, the thickness of the biomechanical pad may range from a thickness that is less that base thickness 108 and increase to a substantially greater thickness, e.g., to provide a biomechanical pad with an effective pad "cut-out" to offload excessive weight-bearing stress in the symptomatic area.

Figure 9:
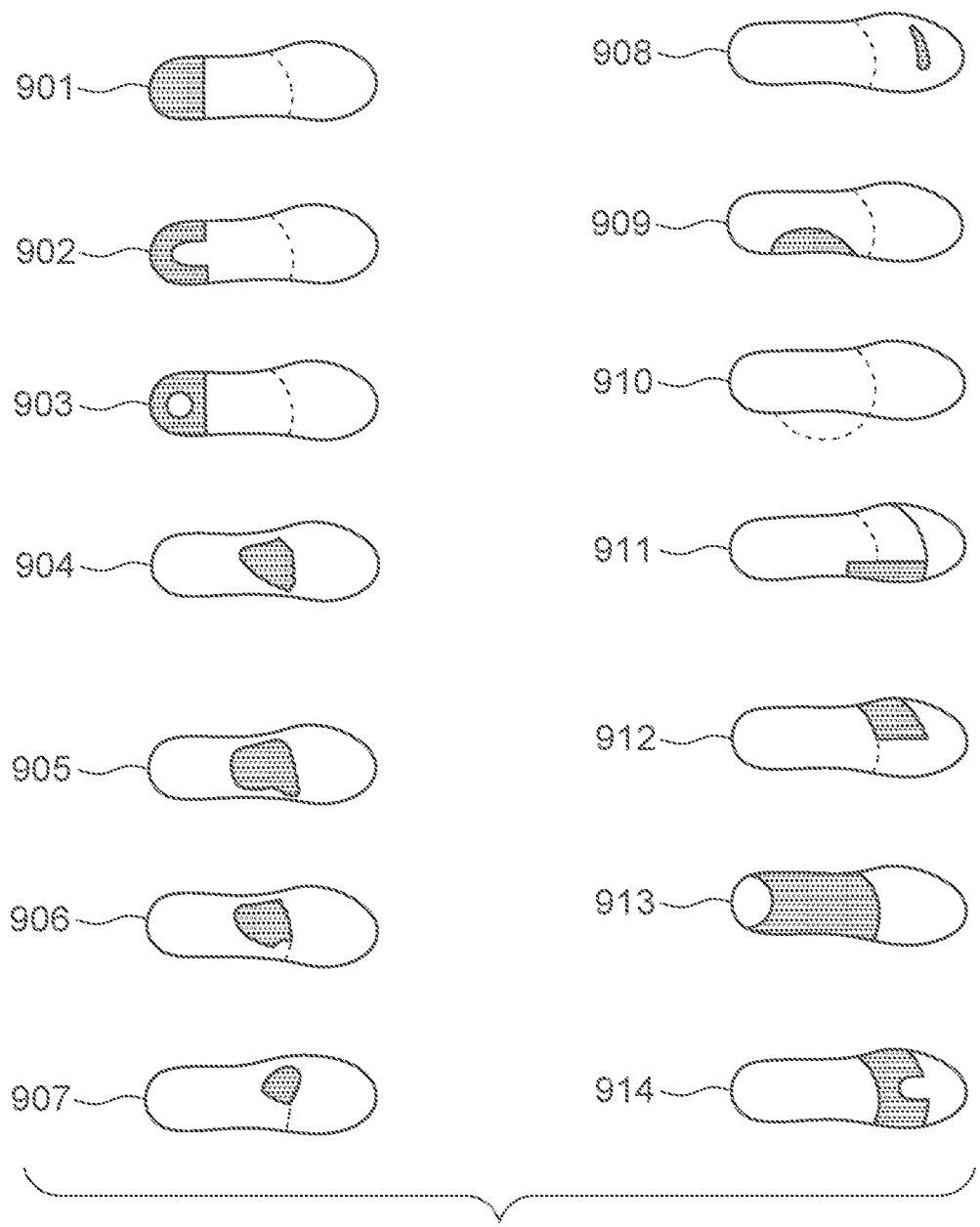
FIG. 9 includes top views illustrating biomechanical pad configurations of the prior art.

As illustrated in FIG. 8A and FIG. 8B, extra padded section 102 and transition section 106 are thicknesses added to sock sole 120. These sections are integrated into sole 120 with the effect that the area of extra padding, e.g., transition section 106 and the section of sole 104 over the distance 122, is unified, i.e., sections 106 and 104 are not distinct this area, though the area may vary in thickness and density. In embodiments, biomechanical pad corrections may extend upward along the inside or outside edge to provide support and compensation for excessive pronation or supination. For example, such a pad configuration may be found in a Carlton saddle (a soft medial flange 913) (FIG. 9). Generally, it should be understood that embodiments may include any biomechanical pad configuration.

FIG. 9 includes top views illustrating biomechanical pad configurations of the prior art. FIG. 9 illustrates the shapes of pads that may be knit into an embodiment of a sock orthotic. Such pads include: a heel lift 901, a heel spur pad 902, a heel cut-out 903, a metatarsal pad 904, a metatarsal bar 905, a dancer's pad 906, a neuroma pad 907, a toe crest 908, a scaphoid pad 909, a soft medial flange 910, a Morton's extension 911, a reverse Morton's extension 912, a Carlton saddle 913, and a metatarsal cut-out 914.

Figure 10:
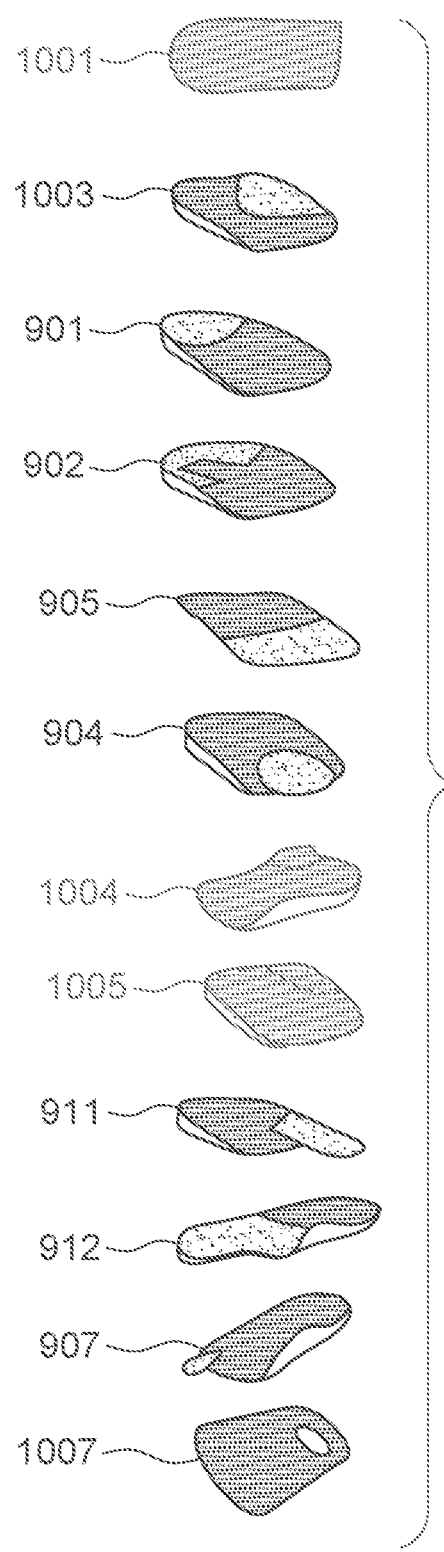
FIG. 10 includes perspectives views illustrating biomechanical pad configurations of the prior art.

FIG. 10 includes perspectives views illustrating biomechanical pad configurations of the prior art. FIG. 10 further illustrates the shapes of pads that may be knit into an embodiment of a sock orthotic. Such pads include: first ray cut-out 1001, first metatarsal cut-out (not shown), an arch pad 1003, heel pad 901, heel spur pad 902, metatarsal bar 905, metatarsal pad 904, lateral flange 1004, medial flange 1005, Morton's extension 911, reverse Morton's extension 912, neuroma pad 907, and a heel cut-out 1007.

Figure 11:
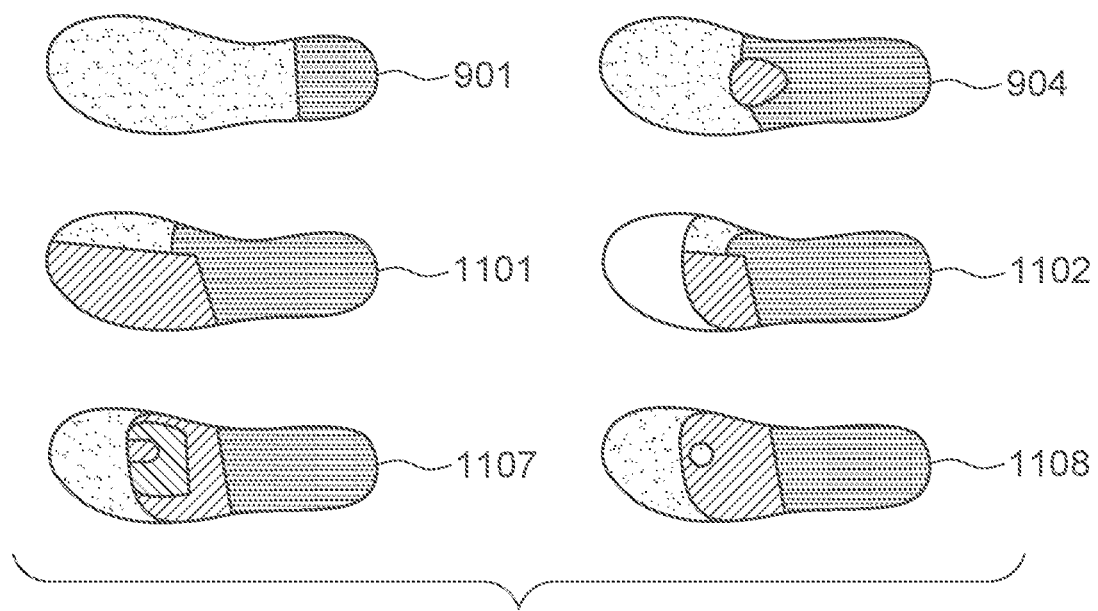
FIG. 11 includes top views illustrating biomechanical pad configurations of the prior art.

FIG. 11 includes top views illustrating biomechanical pad configurations of the prior art. FIG. 11 further illustrates the shapes of pads that may be knit into an embodiment of a sock orthotic. Such pads include: heel pad 901, metatarsal pad 904, reverse Morton's frame-extension to toes 1101, reverse Morton's frame-extension to sulcus 1102, a metatarsal balance pad 1107, and a pad cut-out 1108.

Figure 12:
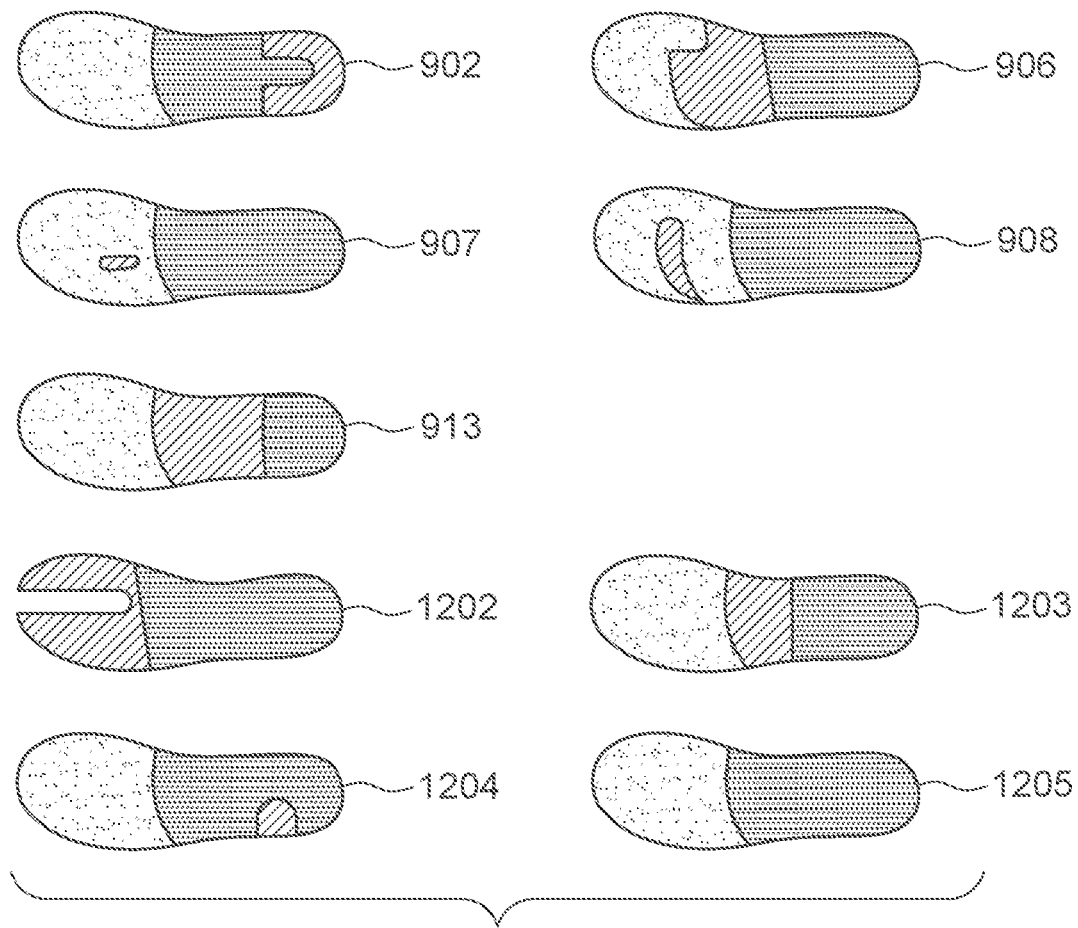
FIG. 12 includes top views illustrating biomechanical pad configurations of the prior art.

FIG. 12 includes top views illustrating biomechanical pad configurations of the prior art. FIG. 12 further illustrates the shapes of pads that may be knit into an embodiment of a sock orthotic. Such pads include: a cut-out pad 1202, a metatarsal bar pad 1203, dancer's pad 906, toe crest pad 908, neuroma pad 907, a cuboid offload 1204, heel spur pad, 902, Carlton saddle 913, and a Valgus onlay pad 1205.

Thus, in embodiments, a sock orthotic may be used to treat a specific condition of the foot by including a knit section in the shape of any of the pad or insert corrections of the prior art associated with the treatment of the specific condition. For example, the following biomechanical correction configurations may be incorporated into an embodiment of a sock orthotic to correct the condition listed:

Varus Wedge: used to correct excessive pronation or flatfoot and treat plantar fasciitis and shin splints, Valgus Wedge: used to correct excessive supination and treat high arch foot, Cobra Pad: used to provide arch support, reduce focal heel pressure, and treat heel spur and plantar fasciitis, Metatarsal Pad: used to relieve focal pressure on areas of the forefoot and treat metatarsalgia;

Neuroma Pad: used to relieve metatarsal pressure on the nerve and treat interdigital neuroma, Dancer's Pad: used to relieve pressure under the great toe joint and treat sesamoiditis or turf toe;

Heel Lift: used to elevate heel and treat Achilles tendonitis or leg length inequality.

In some embodiments, a sock orthotic unit may include some combination of: a right sock orthotic, a left sock orthotic, and a neutral or uncorrected sock. In some embodiments, a sock orthotic may include only a right sock orthotic or a left sock orthotic. In some embodiments, a sock orthotic may be appropriate for either right or left foot.

In an embodiment, extra padded section 102, e.g., sections 102n, may be integrated into sock sole 120 during the knitting process by pulling in additional loops of yarn. These additional loops may vary in length, gauge, and choice of material to achieve the desired properties of the therapeutic extra padded section 102, such as, e.g., a desired thickness, or density. Longer loops may be referred to as "terry." The additional loops may be integrated in combinations of lengths and/or elastic yarns, such as Lycra, to realize the desired functional thickness differential (i.e., extra padded thickness 114) for the area of correction, accommodation, or wedging. The sock orthotic may also have traditional elastic yarn utilized in its fabrication to provide comfort and reduce stretching.

In an embodiment, sole 120 may be marked to indicate the location of the therapeutic area. In an embodiment, sole 120 may be marked to indicate the proper location the metatarsal heads at the ball of the foot, to ensure proper positioning and fit of the sock on the foot. Such marking may be visible on the bottom surface of sole 120, and the top surface of sock upper 110.

In an embodiment, if additional pattern padding is needed, a sock orthotic may be manufactured in two jointly attached "mirror" pattern lengths so that when one half is inverted on itself, two identical areas of pattern padding are superimposed, creating a two layer sock with double layers of configured corrections.

In an embodiment, a single sock orthotic may be reversible for use on either left or right foot. In such an embodiment, extra padded section 114 would be evenly distributed above and below base sole section 104.

The previous description is provided to enable any person skilled in the art to practice the various aspects described herein. In the embodiments, the separation of various system components in the embodiments described above should not be understood as requiring such separation in all embodiments. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A phrase such as a configuration may refer to one or more configurations and vice versa.

All structural and functional equivalents to the elements of the various aspects described throughout this disclosure that are known or later come to be known to those of ordinary skill in the art are expressly incorporated herein by reference and are intended to be encompassed by the claims.

What is claimed is:

1. A sock orthotic comprising
a knitted sock having: a sock upper section; and a sock sole section including at least one knitted pattern, wherein:
the at least one knitted pattern is an intrinsic part of the sock sole section;
at least part of the at least one knitted pattern has a first thickness that is greater than a second thickness of an adjacent part of the sock sole section, thereby forming a padded region within the sock sole section, where the first thickness is at least 1/8" greater than the second thickness when the pad and the adjacent part of the sock sole section are compressed by a user's weight, and the first thickness increases in thickness when uncompressed; and
the at least one knitted pattern has a three-dimensional shape and is located on a transverse plane of the sock sole section such that, when the sock orthotic is worn by a user between a foot of the user and a shoe or a weight-bearing surface, the at least one knitted pattern creates an interface between the foot and the shoe or weight-bearing surface, the interface corrective of a biomechanically abnormal area of the foot of the user by having the at least one knitted pattern first thickness at a location on the transverse plane of the sock sole section that is spaced apart from and not directly underneath the biomechanically abnormal area and not applying elastic compression to the biomechanically abnormal area, the at least one knitted pattern selected from the group consisting of an intrinsically knit varus wedge pattern, an intrinsically knit valgus wedge pattern, an intrinsically knit cobra pad; an intrinsically knit metatarsal pad configured to be located immediately proximal to the metatarsal heads and extending proximally to a mid-arch area of the foot; an intrinsically knit neuroma pad; an intrinsically knit dancer's pad; an intrinsically knit heel spur pad, an intrinsically knit heel cut-out perimeter, an intrinsically knit toe crest, an intrinsically knit Morton's extension, an intrinsically knit reverse Morton's extension, and an intrinsically knit Carlton saddle.

2. The sock orthotic of claim 1, wherein the knitted pattern is formed by pulling in additional loops of yarn.

3. The sock orthotic of claim 2, wherein the additional loops of yarn are different from yarn in the sole in at least one of: length, thickness, gauge, elasticity, or density.

4. The sock orthotic of claim 1, wherein a transition from the surrounding sock thickness to the knitted pattern is a step transition.

5. The sock orthotic of claim 1, wherein a transition from the surrounding sock thickness to the knitted pattern is a ramp transition.

6. A method for treating a biomechanically abnormal area of a foot of a user, the method comprising:
obtaining, by the user, a knitted sock orthotic comprising a sock upper section; and a sock sole section including at least one knitted pattern, wherein:
the at least one knitted pattern is an intrinsic part of the sock sole section;
at least part of the at least one knitted pattern has a first thickness that is greater than a second thickness of an adjacent part of the sock sole section, thereby forming a padded region within the sock sole section; where the first thickness is at least 1/8" greater than the second thickness when the pad and the adjacent part of the sock sole section are compressed by a user's weight, and the first thickness increases in thickness when uncompressed; and
the at least one knitted pattern has a three-dimensional shape and is located on a transverse plane of the sock sole section such that, when the knitted sock is worn by the user between the foot of the user and a shoe or a weight-bearing surface, the at least one knitted pattern creates an interface between the foot and the shoe or the weight-bearing surface, the interface corrective of the biomechanically abnormal area of the foot of the user by having the at least one knitted pattern first thickness at a location on the transverse plane of the sock sole section that is spaced apart from and not directly underneath the biomechanically abnormal area and not applying elastic compression to the biomechanically abnormal area, the at least one knitted pattern selected from the group consisting of an intrinsically knit varus wedge pattern, an intrinsically knit valgus wedge pattern, an intrinsically knit cobra pad; an intrinsically knit metatarsal pad configured to be located immediately proximal to the metatarsal heads and extending proximally to a mid-arch area of the foot; an intrinsically knit neuroma pad; an intrinsically knit dancer's pad; an intrinsically knit heel spur pad, an intrinsically knit heel cut-out perimeter, an intrinsically knit Morton's extension, an intrinsically knit reverse Morton's extension, and an intrinsically knit Carlton saddle; and wearing, by the user, the knitted sock orthotic having a knitted pattern selected from the group to treat the biomechanically abnormal area of the foot.

7. The method of claim 6, wherein the knitted pattern is formed by pulling in additional loops of yarn.

8. The method of claim 7, wherein the additional loops of yarn are different from yarn in the sole in at least one of: length, thickness, gauge, elasticity, or density.

9. The method of claim 6, wherein a transition from the surrounding sock thickness to the knitted pattern is a step transition.

10. The method of claim 6, wherein a transition from the surrounding sock thickness to the knitted pattern is a ramp transition.

* * * * *